United States Patent [19]

Pierce et al.

[11] 4,368,056

[45] Jan. 11, 1983

[54] DIESEL FUEL BY FERMENTATION OF WASTES

[76] Inventors: Sammy M. Pierce, P.O. Box 84, Hamilton, Ill. 62341; Morris Wayman, 17 Noel Ave., Toronto, Ontario, Canada, M4G, 1B2

[21] Appl. No.: 265,451

[22] Filed: May 20, 1981

[51] Int. Cl.$^3$ ............................................... C10L 1/18
[52] U.S. Cl. .......................................... 44/53; 44/57; 44/66
[58] Field of Search ........................... 44/53, 55, 57, 66

[56] References Cited

U.S. PATENT DOCUMENTS

| | | | |
|---|---|---|---|
| 1,420,622 | 6/1922 | Charbonneaux | 44/66 |
| 2,147,487 | 2/1939 | Hall | 435/150 |
| 2,179,151 | 11/1939 | Jean | 44/55 |
| 2,311,929 | 2/1943 | Chenicek | 44/66 |

OTHER PUBLICATIONS

Wayman et al., Canadian Journal of Microbiology, vol. 20, No. 2, 1974, pp. 225–230.
"Vegetable Oil as Diesel Fuel?" J. Am. Oil Chemists Soc. 57, 805-A–811-A, 816A–819A, (Nov. 1980).

*Primary Examiner*—Jacqueline V. Howard
*Attorney, Agent, or Firm*—Zarley, McKee, Thomte, Voorhees & Sease

[57] ABSTRACT

An improved diesel fuel which is entirely capable of preparation from renewable resources. The fuel comprises a blend of fermentation produced butanol and fermentation produced glycerides. The substrates useful for the butanol fermentation are conventional industrial waste products, such as cheese whey and low value carbohydrate containing waste materials such as corn cobs, wood chips, etc. Similar substrate materials are used in the fermentation or growth culture of glyceride producing microbes.

9 Claims, No Drawings

DIESEL FUEL BY FERMENTATION OF WASTES

BACKGROUND OF THE INVENTION

Diesel fuels are traditionally hydrocarbon liquids obtained by the fractionation and refining of petroleum. The cost of petroleum crude oil has been rising very rapidly. The rather drastic increases in crude oil costs have placed a severe burden upon many commercial and industrial operations, using substantial amounts of diesel fuel.

The total amount of diesel fuel used each year in such operations is enormous, with for example, diesel fuel consumption in the United States alone amounting to more than 10 billion gallons in 1980. The rising costs of diesel fuel, coupled with the inevitable depletion of supply, have created serious concern. Thus, there is a real and continuing need for an alternative source of diesel fuel which is available without import dependency, and which can be generated from a renewable resource.

In seeking alternatives to petroleum based diesel fuel, one primary target of investigation has been alcohols. For example, methanol has been a prime object of investigation. However, methanol has met with only limited success as a substitute, because it is currently made on a large scale commercial basis exclusively from natural gas or petroleum. Methanol cannot therefore be regarded as other than in limited supply in the same way as natural gas and petroleum.

In the past, there has been some discussion of use of glycerides as a fuel substitute, that is, vegetable oils such as castor oil, sunflower seed oil and rapeseed oil, see, for example *Journal of American Oil Chemists Society*, Vol. 57, No. 11, November 1980, entitled "Searching for New Diesel Fuels". However, while vegetable oils such as those described in the referenced article do avoid petroleum as a supply source, there are other potential problems. That is, the use of primary human food products for fuel constitutes a sort of competition between use of these as foods or as energy sources for operation of diesel engines. Nevertheless, since we have not yet reached the limits of our agricultural capacity to produce renewable crops such as soybeans, sunflower seeds, rapeseeds, castor beans and the like, the possible use of vegetable oils derived from these seeds for fuel is realistic.

Accordingly, a primary object of this invention is to produce an improved diesel fuel which is wholly prepared from non-petroleum based materials.

Another objective of the present invention is to prepare a diesel fuel from entirely renewable resource materials, all readily available without dependency on foreign imports.

A further object of this invention is to provide a diesel fuel composition which is prepared exclusively from industrial waste materials by a fermentation process.

A yet further objective of the present invention is to produce a diesel fuel composition which is a blend of fermentation produced butanol and vegetable derived glycerides.

An even more particular objective of the present invention is to produce a diesel fuel composition comprising a blend of fermentation produced butanol with a blend of fermentation produced glycerides.

And yet another objective of the invention is to provide a process for making a diesel fuel composition which comprises fermenting cellulosic substrate materials, in the presence of a culture of butanol forming micro-organisms; and growing a culture of glyceride accumulating micro-organisms under suitable culture conditions, followed by extracting both the butanol and the glyceride; and thereafter blending both to provide a diesel fuel.

The method and manner of accomplishing each of the above objectives, as well as others, will become apparent from the detailed description of the invention which follows hereinafter.

SUMMARY OF THE INVENTION

In accordance with this invention, mixtures of products of fermentation are used as diesel fuels. These mixtures contain fermentation produced butanol blended with glycerides, preferably microbial produced glycerides.

Low value carbohydrate containing industrial waste materials such as municipal solid waste, waste paper, distressed grain, agricultural crop residues such as corn cobs and the like, are the fermentation substrate. Butanol fermentation takes place in the presence of butanol forming bacterium such as *Clostridium acetobutylicum* (Weizmann). The growth, or fermentation production of the microbial glycerides takes place in the presence of a culture of glyceride accumulating bacterium such as Arthrobacter AK 19, American Type Culture Collection, Deposit No. 27779.

Since butanol and glycerides are mutually soluble, one in the other, the fermentation produced butanol can be used to extract glycerides from the cells of the glyceride accumulating bacterium to provide the desired blend. The preferred blend ratio of butanol to glycerides is from about 3:1 to 1:3.

DETAILED DESCRIPTION OF THE INVENTION

The diesel fuel composition of this invention comprises a blend of butanol and glycerides, with the ratio of the butanol to the glycerides being within the broader range of from about 10:1 to 1:10, preferably 3:1 to about 1:3. Most preferably the fuel composition has a ratio of butanol to glycerides of from about 2:1 to about 1:2. Of course, as is apparent to those of skill in the art, particular manipulations of the ratio of the respective components within the ranges specified herein, may be accomplished in order to optimize performance.

As mentioned previously, the preferred composition of the present invention comprises a blend of fermentation produced butanol with a blend of glycerides, preferably glycerides produced by glyceride accumulating microorganisms. The glycerides are thereafter extracted from the organism. Thus, it can be seen that the diesel fuel composition of the present invention has the complete capability of being prepared wholly from renewable resource material, available without reliance upon foreign imports. Moreover, the fuel can be made from readily available industrial waste materials, as the fermentation substrate.

Further details of the product will become apparent with regard to the description of the ferment preparation and blending of the individual components. We turn first to the fermentation preparation of the butanol component.

The art of making butanol by fermentation is known. The process for making butanol by fermentation was discovered by Charles Weizmann, after whom the fermenting organism is named, *Clostridium acetobutylicum* (Weizmann). Fermentation processes for the production of butanol are known and described in detail in much published literature and a number of patents. Since the butanol fermentation is known, the details of a representative process need not be described in detail, herein. For examples of patents discussing butanol fermentation processes, see for example, the following U.S. Pat. Nos.: 2,223,788; 2,218,426; 2,377,197; 2,202,785; 4,205,133; 1,875,536; 2,147,487; 2,260,126; and 2,182,989. Each of the butanol fermentation processes and apparatus discussed in these representative state of the art patents, can be used for formation of the fermented butanol useful in this invention. And so, the disclosures of these patents, to the extent that they disclose representative fermenting processes useful for preparation of butanol from bacterium such as *Clostridium acetobutylicum* (Weizmann), are incorporated herein by reference.

As those skilled in the fermentation art know, butanol produced by a fermentation process, such as those mentioned in the above patents, can be purified to produce pure butanol, or an alcohol product mixture can be separated and used. The product mixture which can be separated is predominantly butanol, but does have small amounts of fermentation by-products such as ethanol and acetone. In accordance with the process of this invention, either the purified butanol may be used, or the fermentation butanol, without separating the fermentation by-products. And so, "fermentation butanol" as used herein, refers to a mixture of butanol, acetone and ethanol, which is predominantly butanol.

Briefly, a low cellulose value waste material such as spent grain mashes, molasses, municipal solid waste, waste paper, wood chips, distressed grain, agricultural crop residue such as corn stalks, cobs, straw, bagasse and the like, are suitable carbohydrate containing fermentables useful as the substrate for the butanol production. The fermentable substrate material is mixed with butanol forming bacterium such as *Clostridium acetobutylicum* (Weizmann), or others such as *Clostridium saccharo acetobutylicum,* described in U.S. Pat. No. 2,089,522 of Woodruff, et al; the bacteria of the group *Clostridium inverto acetobutylicum,* described in U.S. Pat. No. 2,089,562 of Legg, et. al; *Clostridium saccharo acetobutylicum-gamma,* described in U.S. Pat. No. 2,050,219 of Arzberger; the bacteria of the group *Clostridium propyl butylicum,* the bacteria of the group *Clostridium saccharo-butyl-acetonicum-liquefaciens,* described in Pat. No. 2,139,108, issued Dec. 6, 1938; and *Clostridium saccharo-butyl-acetonicum-liquefaciens-gamma* and *Clostridium saccharo-butyl-acetonicum-liquefaciens-delta,* described in U.S. Pat. No. 2,139,111 issued Dec. 6, 1938, and *Bacillus butacone* described in U.S. Pat. No. 2,147,487, issued Feb. 14, 1939.

The invention is generally applicable to any bacteria of this butanol forming class, but the starch fermenting bacteria *Clostridium acetobutylicum* (Weizmann) or the *Bacillus butacone,* which is relatively insensitive to the presence of air during fermentation are preferred.

The amount of butanol forming bacterial culture employed can vary from $\frac{1}{2}$% to 10%, preferably from 3% to 7.5% by weight of the fermentable mash and suitable results, for example, can be achieved with a 5% inoculation of the active culture. Suitable fermenting conditions include: maintenance at fermenting temperatures of 20° to 40° C., preferably 25° C. to 35° C., in the presence of well-known bacteria nutrients such as nitrates, acetates, sulfates, and the like, at a pH within the range of 5.0 to 6.5 for from 10 hours to 48 hours, preferably 18 to 36 hours.

The fermented butanol may then be separated by conventional chemical separation techniques such as filtration with filter fermenters such as those described in U.S. Pat. No. 4,205,133, the disclosure of which is incorporated herein by reference. As previously mentioned, the butanol may be used in the form of fermented butanol, or it may be purified to provide pure butanol. However, since the fermented butanol works substantially as well as the purified butanol, there is economic advantage in using the fermented butanol, which is therefore preferred.

Next, we turn to the glyceride component. It can be derived from two separate sources. A first source is by conventional extraction from glyceride containing plant seeds of products such as sunflower seeds, rapeseed, castor beans, soybeans, mustard seed, peanuts, coconuts, cottonseed, rice bran, crambe, etc. If such seed products are used as the glyceride component source, extraction techniques are well known, and need not be described herein.

While vegetable extracted oils can be used, they do bring into play the inevitable conflict between their valuable use as primary human food sources versus their use as fuels. Thus, the primary benefit of this invention can be achieved when the glyceride source is microbial produced glycerides.

Microbial glycerides are generated by growing glyceride accumulating micro-organisms in a nutrient fermenting environment; and thereafter, extracting the glycerides from the micro-organism. Thus, in the overall process of the present invention, two fermentation systems are operated in parallel. Both can utilize similar low value carbohydrate containing substrate materials in the fermentation process. The earlier mentioned industrial wastes are equally suitable substrates in the glyceride fermentation process.

In the glyceride producing process, glyceride accumulating microbes are grown. There are several classes of such glyceride accumulators. They are bacteria, yeasts, and algae. Microbial glyceride production differs markedly from butanol fermentation in that in the latter case, the butanol and other organic products are released into the brew, from which they are recovered. In the case of microbial glycerides, the glycerides remain within the bodies of the microbes. These microbial cells are separated from the growth medium, by filtration or centrifugation, and the glycerides are extracted from the cells by organic solvents, from which they are recovered by solvent evaporation.

Microbial glycerides are soluble in butanol and in the fermented butanol mixture produced by fermentation. To prepare diesel fuel, it is merely necessary to dissolve the appropriate proportion of microbial glycerides in the butanol, or fermentation butanol. The diesel fuel so made may vary somewhat in composition depending upon the specific service it is meant to perform, with altitude, season, particular engine type and other variables. It may also have minor quantities of additives designed to improve performance, reduce corrosion and confer other beneficial properties upon the fuel. These are matters well known to those who formulate such fuels. However, in accordance with this invention the principal components of the fuel to the extent of at least about 85% are a mixture of fermentation butanol and microbial extracted glycerides.

While several glyceride-accumulating microbes are known, a particular bacterium Arthrobacter AK 19 (American Type Culture Collection No. 27779) which, when grown with due care, can accumulate over 80% of its cell substance as glycerides, is preferred. These glycerides are shown to be approximately equal quantities of mono and triglycerides, and about two-thirds to 70% are unsaturated. These glycerides are an excellent diesel fuel component. A useful alternative glyceride accumulating micro-organism is a yeast Candida 107 which has a somewhat smaller yield of glycerides, about 65%, but being a larger micro-organism, it is easier to filter and extract. Other micro-organisms are also known to accumulate glycerides, and these may prove advantageous in some circumstances. Examples include the yeasts Rhodotorula gracilis, and Lipomyces lipofer, and the fungi Aspergillus terreus and Penicillium spinulosum.

Glycerides may be recovered by extraction from the cells of the micro-organisms. In one example, cells of Arthrobacter AK 19 containing 80% of glycerides were extracted with a solvent consisting substantially of methanol, and the glycerides were recovered by evaporation of the solvent. The yield of glycerides can be improved somewhat by physical disruption of the cell walls, by ultrasonics or grinding.

The two components, microbial glycerides and fermentation butanol, having been obtained as described, are readily blended, for example, by pumping separate streams into an in-line mixer or blending device at rates controlled so as to achieve the desired final composition of the diesel fuel. A preferred composition consists of equal quantities of the two components. The blender can also be a convenient device for adding such further minor components to the blend as are desired for improved performance, such as corrosion resistance, and the like.

As heretofore mentioned, the glyceride forming process has from time to time been mentioned as a fermentation process. It may be more accurate to refer to it as a glyceride microbial growth process. However, it should be understood that whatever term is employed, it refers to the process of feeding certain microbes, yeast fungi, algae or bacteria to allow the microbes to grow, and as they grow, they in turn produce intra-cellular glycerides. Thereafter, the cell walls may be disrupted and the glycerides extracted. A typical example of a suitable and preferred glyceride accumulating bacteria is Arthrobacter AK 19, American Type Culture Collection No. 27779. This bacterium was deposited by Dr. Morris Wayman, with the American Type Culture Collection and appears in their catalog. The address for this Culture Collection, which is available to the public on request, is 12301 Park Lawn, Rockville, Md. 20852. An example of a suitable yeast is Candida 107, which is publicly available at the University of Hull, Hull, England, particularly from Professor Colin Ratledge. Other suitable yeasts may be the following: Rhodotorula gracilis and Lipomyces lipofer.

With regard to suitable fungi, those may be selected from the following: Aspergillus terreus and Penicillium spinulosum.

The microbial growth or fermenting conditions, are those suitable for normal culture growth. The temperature is typically within the range of from 20° C. to 40° C., reaction time within the range of from about two to about five days. The suitable substrates useful to grow the bacteria are those same ones previously mentioned with regard to the butanol fermentation.

Certain nutrients may be added to the media composition such as inorganic salts and trace elements, along with buffer compositions such as phosphate buffers. The typical effective pH for the composition can be within the range of five to seven. One very satisfactory source of salts and trace elements are salt compositions taken from the Dead Sea. For an example of a suitable media composition for the microbial growth of glycerides, see the following article, Wayman, et al., *Canadian Journal of Microbiology*, Vol. 20, No. 2, 1974, pp. 225–230, which are incorporated herein by reference.

The amount of the glyceride accumulating bacterium, yeast or fungi culture, may be within the range of from about ½% to about 10% by weight, preferably within the range of from 1% to about 2% by weight.

The following example is offered to further illustrate but not necessarily limit, the preparation and use of the compositions of the invention. In the example, the butanol portion of the blended diesel fuel and the glyceride portion of the blended diesel fuel are both made by cultured media growth processes. In particular, the butanol by a butanol fermentation process and the glyceride by microbial growth of a culture of glyceride accumulating bacterium, Arthrobacter AK 19.

EXAMPLE

Preparation of Fermentation Substrate

A solution of wood sugars for use as substrate is prepared from waste aspen wood as follows. Chipped green aspen wood is treated continuously in a pressure vessel brought to 200° C. by direct steam, at a pressure of 230 psig, with a retention time of six minutes. The steamed wood is exploded from the vessel by the sudden opening of a ball valve for a few seconds of every minute, thereby effecting a sudden decompression. The result is a mass of fibres and fibre bundles highly activated for enzyme action. The exploded wood is suspended in 10 times its weight of 2% sodium hydroxide solution at 50° C., and after thorough soaking, is recovered from suspension by means of a drum filter press. The solution contains lignin, which may be recovered for use or for sale. The fibre is suspended in ten times its weight of water at 50° C., the acidity is adjusted to pH 4.8, and an enzyme mixture is added. The enzyme mixture consists of three commercial enzymes, Novo cellulase, Novo cellobiase, and Miles hemicellulase, in the proportion of 2:1:1. A total of 10% by weight of the enzyme mixture is added and allowed to act with gentle agitation for 24 hours, producing a sugar solution. The unreacted fibre is separated from the sugar solution by a drum filter press, and given a second treatment with fresh enzyme mixture in the same proportion, but prolonged to 48 hours. The so-produced sugar solution is separated from any unreacted fibre as before. The two sugar solutions are combined, to form the substrate for fermentations. The sugar concentration is 3% glucose plus about 0.5% of other fermentable sugars.

Preparation of Fermentation Glycerides

An inoculum of Arthrobacter AK 19 is prepared by growing a culture in a shake flask of 250 ml capacity in substrate prepared as above, with pH adjusted to 6.8, and the following salts added:

| | |
|---|---|
| KNO₃ | 0.25 g. |
| MgSO$_4$.7H$_2$O | 0.25 g. |
| CaCl$_2$.6H$_2$O | 0.25 g. |
| FeEDTA | 0.25 ml of 0.4% solution |
| Dead Sea salt | 0.025 g. |
| Phosphate buffer | 5 ml |

(Phosphate buffer is made by dissolving Na$_2$HPO$_4$.12H$_2$O 107.4 g and KH$_2$PO$_4$ 39 g in 1 liter of water)

The inoculum is grown with gentle agitation at 28° C. for 48 hours. It is then added to 2.5 liters of substrate in a 4 liter New Brunswick Scientific fermenter, the substrate having been adjusted to pH 6.8 and the same salts added in proportion. The fermenter is continuously agitated at moderate speed and a slow stream of air is passed through to ensure adequate aeration. After six days, the fermenter is emptied and the suspension of bacteria is centrifuged. The microorganism so collected is extracted with methanol and the methanol is evaporated to yield 10 g of oily extract. Upon analysis of this oil, it is found to consist mainly of an equal mixture of mono- and tri-glycerides of long chain fatty acids, of which about 67% are unsaturated. Alternatively, fermentation butanol is used to extract the glycerides from the cells.

Preparation of Fermentation Butanol

While many butanol-forming bacteria cultures are available from the American Type Culture Collection, our preferred bacterium, *Bacillus butacone,* is not. However, explicit directions for the isolation of this bacterium are given in U.S. Pat. No. 2,147,487, issued February 14, 1939, page 1, column 2, line 41 to page 2, column 1, line 28. Following the directions given there, spores of this bacillus are prepared. These are stirred into a viscous, warm preparation of carrageen, a gelatinous polymer derived from a seaweed called Irish moss, and the suspension of spores is added dropwise by syringe to a beaker of cold water. The clear 3/16 inch beads so produced are fairly hard. These "immobilized cells" of B. butacone are added to a three foot high glass column 2 inches in diameter to a depth of 2.5 feet. Substrate prepared as previously described is added to fill the column, which is then kept at 37° C. until strong fermentative activity is evident. This step, in which the spores are converted to vegetative cells, requires about 36 hours. Substrate is then passed upwards through the column at the rate of 150 ml per hour. The effluent from the column is collected, and contains butanol, acetone and ethanol in the approximate ratio of 8 to 1 to 1. The solvents are recovered by extracting them from their aqueous solution by means of a glyceride oil.

Preparation of Diesel Fuel

Fermentation glycerides and fermentation butanol prepared as described are mutually soluble in all proportions. Equal parts are mixed and the resultant solution is a diesel fuel. If the fermentation glycerides are extracted from the glyceride-forming microorganism by fermentation butanol and the fermentation butanol is extracted from its brew by means of fermentation glycerides, these solutions are mixed and the proportions adjusted so that there are equal parts of the two major components, or any desired ratio. The resulting solution is a diesel fuel.

What is claimed is:

1. A process for making a diesel fuel which comprises:

fermenting carbohydrate substrate materials in the presence of a culture of butanol forming microorganisms, to provide an alcohol containing fermented product containing predominant amounts of butanol, separating the alcohol component of the fermented mixture;

growing glyceride accumulating micro-organisms in a nutrient solution of carbohydrate materials;

extracting the glycerides from the micro-organisms with a portion of the fermentation produced alcohol component;

and thereafter, mixing said fermentation butanol and said micro-organism derived glycerides, to provide a diesel fuel.

2. The process of claim 1 wherein the butanol forming bacterium is *Clostridiuim Acetylbutylicum,* (Weizmann.)

3. The process of claim 1 wherein said glyceride accumulating micro-organism is *Arthrobacter AK* 19 of the American Type Culture Collection, Deposit No. 27779.

4. The process of claim 1 wherein said fermentation butanol and said microbial accumulated glyceride are mixed within a blended ratio of fermentation butanol to microbial accumulated glyceride of from 3:1 to 1:3.

5. A diesel fuel composition consisting essentially of:

a blend of fermentation butanol and fermentation glycerides, with the ratio of butanol to glycerides being within the range of from about 3:1 to 1:3 and prepared by the process of claim 1.

6. The fuel composition of claim 5 wherein said fermentation butanol is derived from a fermentation system of a culture of the butanol forming bacterium, *Clostridium Acetobutylicum,* (Weizmann).

7. The fuel composition of claim 5 wherein said fermentation glycerides are derived from a fermentation system of a culture of the glyceride accumulating bacterium, *Arthrobacter* AK 19 American Type Culture Collection Deposit No. 27779.

8. The fuel composition of claim 5 wherein said fermentation glyceride is from a fermentation system of a culture of glyceride forming yeast, *Candida* 107.

9. The fuel composition of claim 5 wherein the glycerides are fermentation produced glycerides, produced from a fermenting system of a culture selected from the group consisting of glyceride forming, bacteria, yeasts, fungi, and algae.

* * * * *